(12) United States Patent
Hoyes et al.

(10) Patent No.: US 10,586,691 B2
(45) Date of Patent: Mar. 10, 2020

(54) METHOD OF CORRELATING PRECURSOR AND FRAGMENT IONS USING ION MOBILITY AND MASS TO CHARGE RATIO

(71) Applicant: Micromass UK Limited, Wilmslow (GB)

(72) Inventors: John Brian Hoyes, Stockport (GB); Steven Derek Pringle, Darwen (GB); Farnoush Salarzaei, Cheshire (GB); Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 252 days.

(21) Appl. No.: 15/035,965

(22) PCT Filed: Nov. 11, 2014

(86) PCT No.: PCT/GB2014/053336
§ 371 (c)(1),
(2) Date: May 11, 2016

(87) PCT Pub. No.: WO2015/071650
PCT Pub. Date: May 21, 2015

(65) Prior Publication Data
US 2016/0293391 A1    Oct. 6, 2016

(30) Foreign Application Priority Data

Nov. 12, 2013    (EP) ..................................... 13192589
Nov. 12, 2013    (GB) ................................... 1319958.3

(51) Int. Cl.
*H01J 49/00* (2006.01)
*H01J 49/42* (2006.01)
*G01N 27/62* (2006.01)

(52) U.S. Cl.
CPC ...... *H01J 49/0031* (2013.01); *H01J 49/0045* (2013.01); *H01J 49/421* (2013.01); *G01N 27/622* (2013.01)

(58) Field of Classification Search
CPC .. H01J 49/0031; H01J 49/0036; H01J 49/004; H01J 49/0045; H01J 49/0081; G01N 27/622; G01N 27/624
See application file for complete search history.

(56) References Cited

U.S. PATENT DOCUMENTS

6,744,043 B2 *  6/2004  Loboda ................ G01N 27/622
                                                      250/282
6,960,761 B2    11/2005  Clemmer
(Continued)

*Primary Examiner* — Brooke Purinton (57) ABSTRACT

A method of mass spectrometry is disclosed comprising separating precursor ions using an ion mobility separator such that different precursor ions have different drift times through the on mobility separator; mass filtering said separated precursor ions with a mass filter, wherein the mass to charge ratios of the precursor ions transmitted by the mass filter vary as a function of the drift times of the precursor ions through the ion mobility separator; performing a first mode of operation comprising fragmenting the separated and mass filtered precursor ions in a fragmentation device to form fragment ions; urging the fragment ions through the fragmentation device such that fragment ions derived from different precursor ions that have been separated by the ion mobility separator are maintained spatially separated from each other as they are urged through the fragmentation device; and detecting the fragment ions. The method enables precursor ions to be associated with their related fragment ions more accurately.

19 Claims, 1 Drawing Sheet

(56) References Cited

U.S. PATENT DOCUMENTS

| | | | |
|---|---|---|---|
| 8,884,218 B2* | 11/2014 | Yamaguchi | H01J 49/004 250/281 |
| 9,048,072 B2 | 6/2015 | Claude et al. | |
| 9,048,073 B2 | 6/2015 | Bateman et al. | |
| 9,190,251 B2 | 11/2015 | Green et al. | |
| 2004/0026612 A1* | 2/2004 | Bateman | H01J 49/062 250/281 |
| 2008/0073497 A1* | 3/2008 | Kovtoun | H01J 49/4225 250/282 |
| 2008/0224033 A1* | 9/2008 | Makarov | H01J 49/004 250/287 |
| 2010/0065733 A1 | 3/2010 | Bateman et al. | |
| 2012/0298860 A1* | 11/2012 | Park | H01J 49/0404 250/288 |
| 2015/0041636 A1 | 2/2015 | Giles et al. | |

* cited by examiner

METHOD OF CORRELATING PRECURSOR AND FRAGMENT IONS USING ION MOBILITY AND MASS TO CHARGE RATIO

CROSS REFERENCE TO RELATED APPLICATIONS

This application is the National Stage of International Application No. PCT/GB2014/053336, filed 11 Nov. 2014 which claims priority from and the benefit of United Kingdom patent application No. 1319958.3 filed on 12 Nov. 2013 and European patent application No. 13192589.3 filed on 12 Nov. 2013. The entire contents of these applications are incorporated herein by reference.

BACKGROUND TO THE PRESENT INVENTION

A conventional $MS^e$ analytical technique comprises performing chromatographic separation on a sample to be analysed, ionising the sample to generate precursor ions and then directing the precursor ions into a fragmentation device that is alternated between a low fragmentation mode and a high fragmentation mode. Precursor ions are substantially not fragmented in the low fragmentation mode and are subsequently pass to a mass analyser for mass analysis, whereas precursor ions are fragmented in the high fragmentation mode and the resulting fragment ions are subsequently passed to the mass analyser for mass analysis. The chromatographic retention times that are related to the periods in which the precursor and fragment ions are detected are known and can be used to correlate a precursor ion to a fragment ion. This technique has proven to be particularly useful in analysis that requires unbiased fragmentation approaches and quantitative information. However, this technique provides only limited confidence that the precursor ions are correctly associated with their related fragment ions.

$MS^e$ techniques have been improved by separating the precursor ions according to their ion mobility prior to their fragmentation and maintaining the temporal fidelity of the ion mobility separated precursor ions and of the fragment ions. The elution profile and elution times from the ion mobility separator are then used in conjunction with the chromatographic information so as to improve the confidence of associating precursor ions with their related fragment ions. This technique is commonly known as $HDMS^e$. However, this improved technique still only provides limited confidence that the precursor ions are correctly associated with their related fragment ions.

It is therefore desired to provide an improved method of mass spectrometry and an improved mass spectrometer.

SUMMARY OF THE PRESENT INVENTION

From a first aspect the present invention provides a method of mass spectrometry comprising:

separating precursor ions using an ion mobility separator such that different precursor ions have different drift times through the ion mobility separator;

mass filtering said separated precursor ions with a mass filter, wherein the mass to charge ratios of the precursor ions transmitted by the mass filter vary as a function of the drift times of the precursor ions through the ion mobility separator;

performing a first mode of operation comprising fragmenting or reacting the separated and mass filtered precursor ions in a fragmentation or reaction device to form fragment or product ions; urging the fragment or product ions through the fragmentation or reaction device such that fragment or product ions derived from different precursor ions that have been separated by the ion mobility separator are maintained spatially separated from each other as they are urged through the fragmentation or reaction device; and detecting the fragment or product ions; and performing a second mode of operation in which the separated and mass filtered precursor ions bypass the fragmentation or reaction device, or are transmitted to the fragmentation or reaction device but are substantially not fragmented, wherein the precursor ions are maintained separated according to their ion mobilities as they bypass the fragmentation or reaction device or as they are transmitted through the fragmentation or reaction device, and detecting the precursor ions;

wherein the method is repeatedly alternated between said first mode in which fragment or product ions are generated in the fragmentation or reaction device and are detected, and said second mode in which precursor ions are substantially not fragmented and are detected; and wherein the fragment or product ions detected in the first mode are correlated to precursor ions detected in said second mode.

According to the present invention, the precursor ions are transmitted from the ion mobility separator to the mass filter. The mass filter preserves the ion mobility separation of the precursor ions that it transmits. The precursor ions are then transmitted to the fragmentation or reaction device and are fragmented, or are reacted with other ions or molecules so as to form product ions. The fragment or product ions are maintained separated from each other according to the ion mobility separation that was imparted on their respective precursor ions. It is therefore possible to relatively accurately associate a fragment or product ion with the ion mobility drift time of its precursor ion. As the mass filter only transmits precursor ions having a relatively narrow band of mass to charge ratios at any given drift time, it is possible use the drift time associated with a fragment or product ion in order to relatively accurately determine the mass to charge ratio of the precursor ion that is associated with the fragment ion. Accordingly, it is possible to associate a fragment ion with its respective precursor ion relatively accurately.

The present invention is advantageous over the conventional $HDMS^e$ techniques described above, since the present invention mass filters the precursor ions in conjunction with ion mobility separation. This enables the fragment ions to be associated with a relatively narrow range of precursor ions transmitted by the mass filter. The present invention therefore enables fragment ions to be associated with their respective precursor ions more accurately.

Preferably, the step of mass filtering the separated precursor ions does not perform charge state selection. In other words, the step of varying the mass to charge ratios of the precursor ions transmitted by the mass filter as a function of drift times preferably does not cause only ions of selected charge states to be transmitted by the mass filter.

In said first mode, electric potentials may be applied to said fragmentation or reaction device, or an axial electric field may be arranged along the fragmentation or reaction device, such that the fragment or product ions are maintained separated from each other according to the on mobilities of their precursor ions.

In said first mode, an axial electric field may be applied along the fragmentation or reaction device so as to perform said step of urging the fragment or product ions through the fragmentation or reaction device such that the fragment or product ions are maintained separated from each other.

In the first mode, fragment or product ions derived from different precursor ions that have been separated by the ion mobility separator may be maintained spatially separated from each other by one or more potential barriers or wells, and said potential barriers or wells may be moved along the fragmentation or reaction device so as to drive the fragment or product ions through the fragmentation or reaction device.

The one or more potential barriers or wells are preferably generated towards the entrance of the fragmentation or reaction device and move in a direction towards the exit of the fragmentation or reaction device so as to drive the fragment or product ions towards the exit.

The fragmentation or reaction device generates first fragment or product ions from a first precursor ion having a first combination of IMS drift time and mass to charge ratio, and generates second fragment or product ions that are derived from a second precursor ion having a second, different combination of IMS drift time and mass to charge ratio; and said first fragment or product ions are preferably separated from said second fragment or product ions by one of said potential barriers of wells. The fragmentation or reaction device may generate third fragment or product ions from a third precursor ion having a third combination of IMS drift time and mass to charge ratio; and the third fragment or product ions may be separated from said first and second fragment or product ions by one of said potential barriers of wells. Fourth and further fragment or product ions may be generated from fourth and further precursor ions in a similar manner, and these fragment or product ions may be maintained separated from other fragment or product ions by one of said potential barriers of wells. Fragment or product ions may be generated from any number of different precursor ions and maintained separated by any number of potential wells or barriers.

The potential barriers or wells are preferably generated and conveyed along and towards the exit of said fragmentation or reaction device in a manner such that fragment or product ions from different separated precursor ions are urged through the fragmentation or reaction device by different potential barriers or wells.

The amplitude of the potential barriers or wells may vary as a function of the position of the potential barriers or wells along the fragmentation or reaction device. For example, the amplitude may increase and/or decrease as a function of position along the device. Alternatively, or additionally, the speed of the potential barriers or wells may vary as a function of the position of the potential barriers or wells along the fragmentation or reaction device. For example, the speed may increase and/or decrease as a function of position along the device.

In said second mode, the precursor ions may be maintained separated from each other as they are transmitted through the fragmentation or reaction device by applying an axial electric field along the fragmentation or reaction device that maintains the precursor ions separated from each other. In the alternative, wherein the ions bypass the fragmentation or reaction device, the precursor ions may be maintained separated from each other by applying an axial electric field along the bypass region so as to maintain the precursor ions separated from each other.

In said second mode, different precursor ions that have been separated by the ion mobility separator may be maintained spatially separated from each other by one or more potential barriers or wells, and said potential barriers or wells may be moved along the fragmentation or reaction device so as to drive the precursor ions through the fragmentation or reaction device. In the alternative, wherein the ions bypass the fragmentation or reaction device, the precursor ions may be maintained separated from each other by one or more potential barriers or wells, and wherein said potential barriers or wells are moved along the bypass region so as to drive the precursor ions through the fragmentation or reaction device.

The precursor ions and/or fragment or product ions exit the fragmentation or reaction device and are preferably then mass analysed.

A fragment or product ion may be correlated to its precursor ions by detecting the fragment or production; determining a drift time or range of drift times through the ion mobility separator of a precursor ion that led to said fragment or product ion being generated and detected; determining the mass to charge ratio or range of mass to charge ratios transmitted by said mass filter substantially at said drift time or range of drift times; and correlating the fragment or product ion with a precursor ion having said mass to charge ratio or being within said range of mass to charge ratios.

The fragment or product ions that are mass analysed and/or detected in the first mode may be associated with the elution times at which their respective precursor ions eluted from the ion mobility separator. The precursor ions that are mass analysed and/or detected in the second mode may be associated with their elution times from the ion mobility separator. The fragment or product ions detected in the first mode may be correlated with their respective precursor ions detected in the second mode by matching the elution times associated with the fragment or product ions with the elution times associated with the precursor ions.

The method may further comprise identifying a precursor ion from one or more fragment or product ion determined to be associated with the precursor ion.

The mass to charge ratios of the precursor ions transmitted by the mass filter may vary as a function of ion mobility separator drift time in a substantially continuous manner; or in a stepped manner.

The precursor ions are preferably pulsed into the ion mobility separator and the mass to charge ratio transmittal window of the mass filter is preferably scanned or stepped as the precursor ions emerge from the ion mobility separator.

The precursor ions are preferably pulsed into the ion mobility separator in a plurality of pulses of precursor ions. The mass to charge ratio transmittal window of the mass filter may be scanned or stepped with drift time as the precursor ions from each pulse emerge from the ion mobility separator; and the mass to charge ratio transmittal window of the mass filter may be scanned or stepped with drift time in a different manner for each pulse of ions pulsed into the ion mobility separator.

Alternatively, the mass filter may be operated with the same scan (or stepped) function for different pulses of precursor ions.

Ions may be pulsed into the on mobility separator a plurality of times. A first pulse of ions may be pulsed into the ion mobility separator and the ions separated therein and a second pulse of ions may be subsequently pulsed into the ion mobility separator and the ions separated therein. The mass to charge ratios of the ions transmitted by the mass filter may vary as a function of ion mobility separator drift time according to a first function for the ions from the first ion pulse, and may vary as a second different function for the ions from the second pulse. Third or further pulses of ions may be provided and the mass filter may vary according to a third or further function respectively. The number of ion pulses and the mass filter functions may be selected such that ions of all mass to charge ratios within the pulses will be passed by the mass filter in the cumulative mass filter functions.

The mass to charge ratios transmitted by the mass filter may, less preferably, be varied as a function of ion mobility separator drift time such that only ions of a particular charge state or only ions of a predetermined range of charge states are transmitted by the mass filter to the fragmentation device.

The precursor ions may be induced to fragment in the fragmentation device by accelerating the ions into the fragmentation device with sufficient energy such that the ions interact with a gas in the fragmentation device and fragment. Less preferably, the precursor ions may be induced to oscillate within a collision gas arranged in the fragmentation device such that the precursor ions fragment. Precursor ions having different drift times through the ion mobility separator may be subjected to different fragmentation energies so as to cause them to fragment. For example, precursor ions having a first IMS drift time may be accelerated into the fragmentation device with a first energy or using a first acceleration voltage difference such that the ions fragment in the fragmentation device; and precursor ions having a second IMS drift time may be accelerated into the fragmentation device with a second, different energy or using a second different acceleration voltage difference such that the ions fragment in the fragmentation device. If ions are induced to oscillate so as to fragment them then precursor ions having a first IMS drift time may be caused to oscillate into fragmentation by an oscillating electric field having a first frequency and/or amplitude, and precursor ions having a second IMS drift time may be caused to oscillate into fragmentation by an oscillating electric field having a second frequency and/or amplitude. Other methods of fragmentation are also contemplated.

The mass filter may comprise an RF quadrupole and a DC resolving voltage. Less preferably, the mass filter may be an RF only quadrupole having a low mass cut off that acts as the mass filter.

Although a quadrupole mass filter is primarily described herein, other types of mass filter are contemplated for performing the same function. For example, the ions may be received from the ion mobility separator in an ion trap and the ion trap may subsequently mass selectively eject ions into the fragmentation or reaction device. The ion trap therefore mass filters the ions that reach the fragmentation or reaction device. Alternative types of filter are also contemplated, such as the use of a time of flight device that separates ions according to their time of flight and transmits only ions having selected flight times.

Although it has been described that the precursor ions are separated by ion mobility separation through a gas, it is contemplated that the ions may alternatively be separated according to Field Asymmetric Ion Mobility Separation (FAIMS), or according to a physico-chemical property other than ion mobility or FAIMS.

Accordingly, from a second aspect the present invention provides a method of mass spectrometry comprising:

separating precursor ions according to a physico-chemical property other than mass to charge ratio;

mass filtering precursor ions according to their mass to charge ratio with a mass filter, wherein the mass to charge ratios of the precursor ions transmitted by the mass filter vary with time;

performing a first mode of operation comprising fragmenting or reacting the separated and mass filtered precursor ions in a fragmentation or reaction device to form fragment or product ions; urging the fragment or product ions through the fragmentation or reaction device such that fragment or product ions derived from different precursor ions that have been separated according to said physico-chemical property are maintained spatially separated from each other as they are urged through the fragmentation or reaction device; and detecting the fragment or product ions;

performing a second mode of operation in which the separated and mass filtered precursor ions bypass the fragmentation or reaction device, or are transmitted to the fragmentation or reaction device but are substantially not fragmented, wherein the precursor ions are maintained separated according to said physico-chemical property as they bypass the fragmentation or reaction device or as they are transmitted through the fragmentation or reaction device, and detecting the precursor ions;

wherein the method is repeatedly alternated between said first mode in which fragment or product ions are generated in the fragmentation or reaction device and are detected, and said second mode in which precursor ions are substantially not fragmented and are detected; and wherein the fragment or product ions detected in the first mode are correlated to precursor ions detected in said second mode.

Preferably, the mass to charge ratios of the precursor ions transmitted by the mass filter vary with time as a function of the first physico-chemical property.

The method according to the second aspect may further comprise any one or combination of the optional or preferred features described above in relation to the first aspect of the present invention, except wherein the ion mobility separator is replaced by a device for separating precursor ions according to physico-chemical property other than mass to charge ratio and ion mobility through a gas.

For example, the precursor ions may be separated according to said physico-chemical property by a FAIMS device.

It is contemplated that the method may not be alternated between said first and second modes.

It is also contemplated that in less preferred embodiments of both the first and second aspects of the present invention, the mass filtering may be performed prior to the ion mobility separation or prior to the separation according to said physico-chemical property. In such an embodiment of the first aspect, the mass filter is varied with time, rather than being varied as a function of drift time through the ion mobility separator.

According to another aspect the present invention provides a mass spectrometer arranged and configured to perform any one of the methods described herein.

Accordingly, the present invention provides a mass spectrometer comprising:

an ion mobility separator;
a mass filter;
fragmentation or reaction device;
an ion detector or mass analyser; and
a controller arranged and adapted to control the spectrometer to;

separate precursor ions using said ion mobility separator such that different precursor ions have different drift times through the ion mobility separator;

mass filter said separated precursor ions with said mass filter, wherein the mass to charge ratios of the precursor ions transmitted by the mass filter vary as a function of the drift times of the precursor ions through the ion mobility separator;

operate the spectrometer in a first mode comprising fragmenting or reacting the separated and mass filtered precursor ions in said fragmentation or reaction device to form fragment or product ions; urge the fragment or product ions through the fragmentation or reaction device such that fragment or product ions derived from different precursor ions that have been separated by the ion mobility separator are maintained spatially separated from each other as they are urged through the fragmentation or reaction device; and detect the fragment or product ions with said detector or mass analyser;

operate the spectrometer in a second mode of operation in which the separated and mass filtered precursor ions bypass the fragmentation or reaction device, or are transmitted to the fragmentation or reaction device but are substantially not fragmented, wherein the precursor ions are maintained separated according to their ion mobilities as they bypass the fragmentation or reaction device or as they are transmitted through the fragmentation or reaction device, and detect the precursor ions with a detector or mass analyser;

repeatedly alternate between said first mode in which fragment or product ions are generated in the fragmentation or reaction device and are detected, and said second mode in which precursor ions are substantially not fragmented and are detected; and to correlate the fragment or product ions detected in the first mode to precursor ions detected in said second mode.

The present invention also provides a mass spectrometer comprising:

an ion separator;
amass filter;
fragmentation or reaction device;
an ion detector or mass analyser; and
a controller arranged and adapted to control the spectrometer to:

separate precursor ions according to a physico-chemical property other than mass to charge ratio in said separator;

mass filter precursor ions according to their mass to charge ratio with said mass filter, wherein the mass to charge ratios of the precursor ions transmitted by the mass filter vary with time;

operate the spectrometer in a first mode comprising fragmenting or reacting the separated and mass filtered precursor ions in said fragmentation or reaction device to form fragment or product ions; urge the fragment or product ions through the fragmentation or reaction device such that fragment or product ions derived from different precursor ions that have been separated according to said physico-chemical property are maintained spatially separated from each other as they are urged through the fragmentation or reaction device; and detect the fragment or product ions;

operate the spectrometer in a second mode in which the separated and mass filtered precursor ions bypass the fragmentation or reaction device, or are transmitted to the fragmentation or reaction device but are substantially not fragmented, wherein the precursor ions are maintained separated according to said physico-chemical property as they bypass the fragmentation or reaction device or as they are transmitted through the fragmentation or reaction device; and detect the precursor ions with a detector or mass analyser;

repeatedly alternate between said first mode in which fragment or product ions are generated in the fragmentation or reaction device and are detected, and said second mode in which precursor ions are substantially not fragmented and are detected; and to correlate the fragment or product ions detected in the first mode to precursor ions detected in said second mode.

The mass spectrometer may comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") on source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") on source; (x) a Field Ionisation ("FI") on source (xi) a Field Desorption ("FD") ion source; (xii) an Inductively Coupled Plasma ("ICP") on source; (xiii) a Fast Atom Bombardment ("FAB") on source; (xiv) a Liquid Secondary ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") on source; (xx) a Glow Discharge ("GD") on source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; and (xxvi) a Solvent Assisted Inlet Ionisation ("SAII") ion source; and/or (b) one or more continuous or pulsed ion sources; and/or
(c) one or more ion guides; and/or
(d) one or more ion mobility separation devices and/or one or more Field Asymmetric Ion Mobility Spectrometer devices; and/or
(e) one or more ion traps or one or more ion trapping regions; and/or
(f) one or more collision, fragmentation or reaction cells selected from the group consisting of (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an on trap mass analyser; (vi) a magnetic sector mass analyser; (vii) on Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole on trap; (iv) a Penning ion trap; (v) an on trap; (vi) a magnetic; sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and an orbitrap (RTM) mass analyser comprising an outer barrel-like electrode and a coaxial inner spindle-like electrode, wherein in a first mode of operation ions are transmitted to the C-trap and are then injected into the orbitrap (RTM) mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the orbitrap (RTM) mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The present invention also provides a method of mass spectrometry comprising:

separating precursor ions using an ion mobility separator such that different precursor ions have different drift times through the ion mobility separator;

mass filtering said separated precursor ions with a mass filter, wherein the mass to charge ratios of the precursor ions transmitted by the mass filter vary as a function of the drift times of the precursor ions through the ion mobility separator; and performing a first mode of operation comprising fragmenting the separated and mass filtered precursor ions in a fragmentation device to form fragment ions; urging the fragment ions through the fragmentation device such that fragment ions derived from different precursor ions that have been separated by the ion mobility separator are maintained spatially separated from each other as they are urged through the fragmentation device; detecting the fragment ions.

This method may have any one, or any combination of any two or more, of the preferred or optional features described in relation to the first aspect of the present invention.

The present invention also provides a mass spectrometer comprising:

an ion mobility separator for separating precursor ions such that different precursor ions have different drift times through the ion mobility separator;

a mass filter for filtering said separated precursor ions, wherein the mass to charge ratios of the precursor ions transmitted by the mass filter vary as a function of the drift times of the precursor ions through the ion mobility separator;

a fragmentation device for fragmenting the separated and mass filtered precursor ions to form fragment ions;

means for urging the fragment ions through the fragmentation device such that fragment ions derived from different precursor ions that have been separated by the ion mobility separator are maintained spatially separated from each other as they are urged through the fragmentation device; and a detector for the fragment ions.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENT

Figure 1:
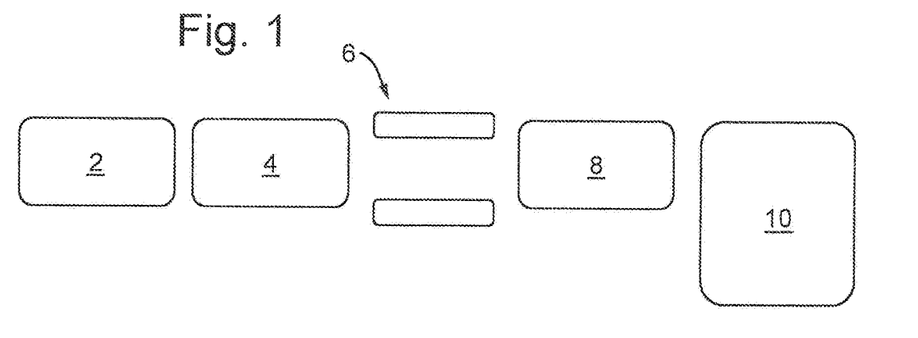
FIG. 1 shows a schematic of a preferred embodiment of the present invention.

FIG. 1 shows a schematic of a preferred embodiment of the present invention. This embodiment comprises an ion source 2, an ion mobility separator (IMS) 4, a quadrupole mass filter 6, a fragmentation device 8 and a Time of Flight mass analyser 10.

In operation, ions are generated by the ion source 2 and are directed into the IMS device 4. Ions having different mobilities pass through the gas in the IMS device 4 with different drift times and so the IMS device 4 causes the ions to separate according to their ion mobility through the IMS device 4. The quadrupole mass filter 6 is arranged between the IMS device 4 and the fragmentation device 8 and only transmits ions having a restricted range of mass to charge ratios at any given time. The mass to charge ratio transmission window of the quadrupole mass filter 6 is scanned with time whilst the ions emerge from the IMS device 4 such that the mass filter 6 mass selectively transmits ions from the IMS device 4 to the fragmentation device 8. Ions are preferably pulsed into the IMS device 4 and the IMS device 4 performs a separation cycle on each group of ions pulsed into the IMS device 4. The mass to charge ratio transmission window of the quadrupole mass filter 6 is preferably scanned during each IMS device cycle so as to selectively filter ions, as will be described in more detail below with reference to FIG. 3.

The fragmentation device 8 comprises means for maintaining the temporal fidelity of the ions that are received at the fragmentation device 8. In other words, the temporal separation of the ions that has been introduced by the IMS device 4 is preserved by the fragmentation device 8. This may be achieved by the use of an axial electric field in the fragmentation device 8. Alternatively, electrical potential wells or barriers may be travelled along the fragmentation device 8 in order to retain the separation of the ions.

The fragmentation device 8 may be operated in a low fragmentation mode wherein precursor ions are substantially not fragmented and are simply transmitted through the fragmentation device 8 to the Time of Flight mass analyser 10. The fragmentation device 8 may also be operated in a high fragmentation mode wherein precursor ions are fragmented and the fragment ions are transmitted through the fragmentation device 8 to the Time of Flight mass analyser 10. In the low fragmentation mode, an axial electric field may be provided along the fragmentation device 8 so as to preserve the temporal separation of the precursor ions that has been imparted to the precursor ions by the IMS device 4. Alternately, the separation may be retained by travelling one or more potential wells or barriers along the fragmentation device 8. For example, a potential well or barrier may be travelled in a direction from the entrance to the exit of the fragmentation device 8 in a manner such that precursor ions of a first ion mobility that are received in the fragmentation device 8 at a first time are separated from precursor ions of a second ion mobility that are later received in the fragmentation device 8 by a potential well or barrier. Ions of a third ion mobility will be received at the fragmentation device 8 even later and these ions are maintained separate from the ions of second ion mobility by a second potential well or barrier. Any number of potential barriers or wells may be used to maintain the separation of any number of different groups of ion mobility as the precursor ions pass through the fragmentation device 8. The potential wells or barriers may be translated along the fragmentation device 8 such that the ion mobility separation is preserved until the precursor ions leave the fragmentation device 8 and pass into the Time of Flight mass analyser 10 to be analysed.

In the high fragmentation mode, the precursor ions are fragmented within the fragmentation device 8 and the resulting fragment ions are transmitted through the fragmentation device 8 to the Time of Flight mass analyser 10. The fragment ions are maintained separated from each other according to the ion mobility of their respective precursor ions as they pass through the fragmentation device 8. In other words, the fragment ions derived from precursor ions of one ion mobility are maintained separated from fragment ions derived from precursor ions of another ion mobility. This may be achieved by providing an axial electric field along the fragmentation device 8. Alternately, the separation may be retained by travelling one or more potential wells or barriers along the fragmentation device 8. For example, a potential well or barrier may be travelled in a direction from the entrance to the exit of the fragmentation device 8 in a manner such that fragment ions that are derived from precursor ions of a first ion mobility are separated from fragment ions that are derived from precursor ions of a second ion mobility by a potential well or barrier. Fragment ions that are derived from precursor ions of a third ion mobility are maintained separate from the other fragment ions by a second potential well or barrier. Any number of potential barriers or wells may be used to maintain the separation of any number of different groups of fragment ions as the fragment ions pass through the fragmentation device. The potential wells or barriers may be translated along the fragmentation device 8 such that the separation is preserved until the fragment ions leave the fragmentation device 8 and pass into the Time of Flight mass analyser 10 to be analysed.

The fragmentation device 8 may be repeatedly alternated between the low fragmentation mode and the high fragmentation mode, in an $MS^e$ experiment. The ion signal profile for the precursor ions varies as a function of the drift time through the IMS device 4. The ion signal profile for a fragment ion can be matched to the ion signal profile for the precursor ions. This enables a fragment ion to be associated with an IMS drift time of its related precursor ion. As the mass filter 6 mass selectively transmits precursor ions as a function of IMS drift time, the IMS drift time that is associated with the fragment ion can be used to determine the mass to charge ratio of the precursor ion that is associated with the fragment ion. The precursor ion associated with the fragment ion can therefore be identified with high confidence.

FIGS. 2 and 3 illustrate the advantages of the present invention over conventional $HDMS^e$ techniques.

According to conventional $HDMS^e$ techniques, the fragmentation device is alternated relatively quickly between high and low fragmentation modes as the precursor ions elute from the IMS device into the fragmentation device. By alternating the fragmentation modes in this manner, precursor ions are not fragmented and are simply mass analysed in the low fragmentation mode, whereas substantially the same precursor ions may be fragmented and the resulting fragment ions mass analysed in a subsequent (or preceding) high fragmentation mode. The ion signal profile for the precursor ions varies as a function of the drift time through the IMS device. The ion signal profile for a fragment ion can be matched to the ion signal profile for the precursor ions. This enables a fragment ion to be correlated to the IMS drift time of its related precursor ion. The mass to charge ratio of a precursor ion is also related to the IMS drift time and hence this technique can be used to correlate the fragment ions to the mass to charge ratio of a precursor ions. However, the degree of certainty of such a correlation is relatively low, as will be described below with reference to FIGS. 2A and 2B.

Figure 2A:
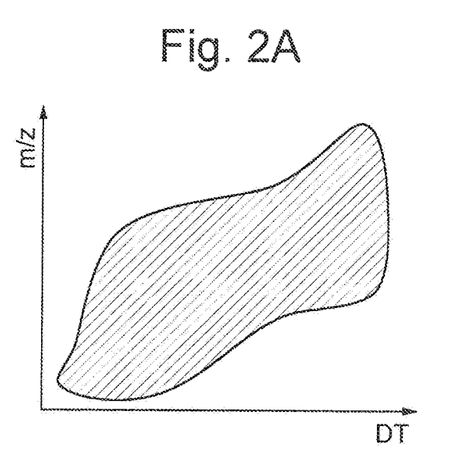
FIG. 2A illustrates the distribution of ions leaving the ion mobility separator in a conventional HDMS$^e$ instrument, and FIG. 2B exemplifies how this may be used to correlate precursor and fragment ions by conventional methods.
Figure 2B:
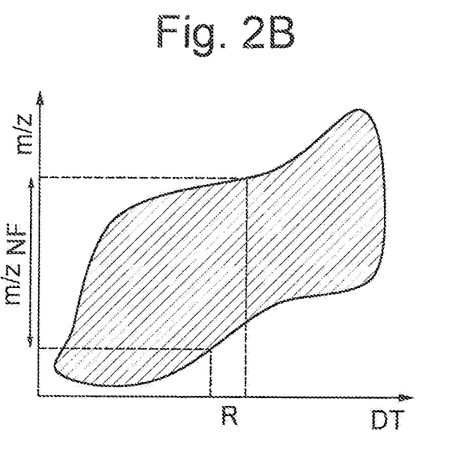

FIG. 2A illustrates the mass to charge ratios of the ions leaving the IMS device and passing into the fragmentation device as a function of drift time through the IMS device in a conventional HDMS$^e$ technique. It will be observed that ions having a relatively wide range of mass to charge ratios exit the IMS device at any given drift time. As described above, a given fragment ion can be correlated to the approximate drift time of its corresponding precursor ion relatively easily. However, it still remains difficult to accurately identify the precursor ion from this information. Referring to FIG. 2B, it may be known that a given fragment ion is correlated to a precursor ion having a drift time through the IMS device that is within the range R. It will be seen that the range of drift times R can only be correlated to a relatively large range of mass to charge ratios for the precursor ion m/$z_{NF}$. As such, it is not possible, according to conventional HDMS$^e$ techniques, to accurately correlate fragment ions with their corresponding precursor ions.

Figure 3A:
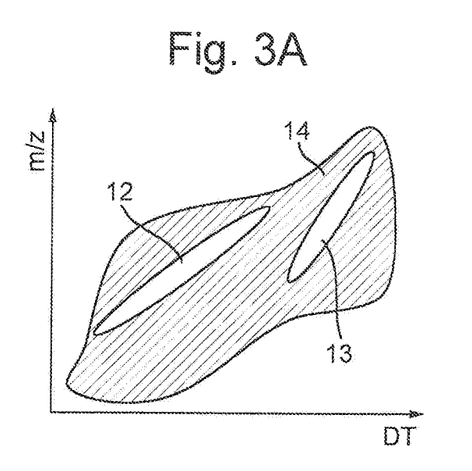
FIG. 3A illustrates the distribution of ions leaving the mass filter in the preferred embodiment of the present invention, and FIG. 3B exemplifies how this may be used to correlate precursor and fragment ions according to the preferred embodiment.
Figure 3B:
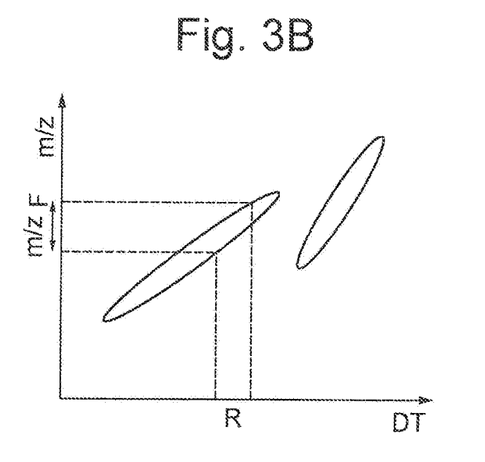

FIGS. 3A and 33 illustrate the effect of an embodiment of the present invention, which includes a quadrupole mass filter 6 between the IMS device 4 and the fragmentation device 8. FIG. 3A shows two regions 12,13 that represent plots of the mass to charge ratios of ions transmitted by the quadrupole mass filter 6, as a function of their drift times through the IMS device 4. The area 14 surrounding the two plots 12,13 represents the ion distribution entering the mass filter 6, which is the same as the distribution of ions leaving the IMS device 4 and which is shown in FIG. 2A. It will be observed from FIG. 3A that the mass filter 6 mass selectively transmits only a relatively narrow range of mass to charge ratios at any given drift time. This improves the accuracy with which fragment ions can be associated to precursor ions, as illustrated with reference to FIG. 3B. For example, it may be known that a given fragment ion is correlated to a precursor ion having a drift time through the IMS device 4 that is within the range R. It will be appreciated that the preferred embodiment enables the range of drift times R to be correlated to a relatively small range of mass to charge ratios for the precursor ion m/$z_F$. As such, the preferred embodiment of the present invention enables one to relatively accurately correlate fragment ions with their corresponding precursor ions.

The preferred embodiment removes undesired precursor ions that have similar IMS drift times to desired precursor ions prior to fragmentation. This removes distracting precursor and fragment ions from the HDMS$^e$ experiment as thus improves the confidence of precursor ion to fragment ion assignment, as compared to conventional HDMS$^e$ techniques.

Although the present invention has been described with reference to preferred embodiments, it will be understood by those skilled in the art that various changes in form and detail may be made without departing from the scope of the invention as set forth in the accompanying claims.

For example, the mass to charge ratios transmitted by the mass filter 6 may be varied as a function of IMS drift time such that only ions of a particular charge state or only ions of a predetermined range of charge states are transmitted by the mass filter 6 to the fragmentation device 8, e.g. as described in U.S. Pat. No. 7,586,088.

Preferably, the range of mass to charge ratios transmitted by the mass filter 6 at any given drift time is smaller than the range of mass to charge ratios that is within the mass filter 6 at that drift time.

A Time of Flight mass analyser 10 is preferred and the present invention may be employed in combination with other established Time of Flight enhancements such as EDC/HDC. However, it is also contemplated that types of mass analyser other than a Time of Flight mass analyser may be used in the present invention. For example, an analytical quadrupole mass analyser with ion detector may replace the Time of Flight mass analyser in an IMS-Q-Q arrangement.

Although the mass filter 6 has been described above as being arranged after the IMS device 4, it is contemplated that in less preferred arrangements the IMS device 4 may be arranged after the mass filter 6, i.e. in a Q-IMS-ToF geometry.

It has been described hereinabove that the ions are separated according to their ion mobility through a gas in an IMS device 4. However, alternative modes of separation are contemplated, such as Field Asymmetric Ion Mobility Separation (FAIMS) or separation by other physico-chemical properties of the precursor ions.

It is also contemplated that the invention may be used in techniques other than MS$^e$ techniques so as to improve the association between precursor and fragment ions.

The invention claimed is:

1. A method of mass spectrometry comprising:
    separating precursor ions using an ion mobility separator such that different precursor ions have different drift times through the ion mobility separator;
    mass filtering said ion mobility separated precursor ions from a single separation cycle of the ion mobility separator with a mass filter, wherein the mass to charge ratios of the precursor ions transmitted by the mass filter vary as a function of the drift times of the precursor ions through the ion mobility separator; and
    repeatedly alternating between performing a first mode of operation and performing a second mode of operation on the ion mobility separated and mass filtered precursor ions from the single separation cycle of the ion mobility separator;
    wherein performing the first mode of operation comprises:
        fragmenting or reacting the ion mobility separated and mass filtered precursor ions in a fragmentation or reaction device to form fragment or product ions;
        urging the fragment or product ions through the fragmentation or reaction device such that fragment or product ions derived from different precursor ions that have been separated by the ion mobility separator are maintained spatially separated from each other as they are urged through the fragmentation or reaction device; and
        detecting the fragment or product ions; and
    performing the second mode of operation comprises:
        the ion mobility separated and mass filtered precursor ions bypassing the fragmentation or reaction device, or being transmitted to the fragmentation or reaction device but being substantially not fragmented;
        maintaining the ion mobility separated and mass filtered precursor ions separated according to their ion mobilities as they bypass the fragmentation or reaction device or as they are transmitted through the fragmentation or reaction device; and
        detecting the ion mobility separated and mass filtered precursor ions; and
    the method further comprising:
    associating fragment or product ions detected when performing the first mode of operation to ion mobility separated and mass filtered precursor ions detected when performing the second mode of operation.

2. The method of claim 1, wherein the step of mass filtering the ion mobility separated precursor ions does not perform charge state selection.

3. The method of claim 1, wherein in said first mode electric potentials are applied to said fragmentation or reaction device, or an axial electric field is arranged along the fragmentation or reaction device, such that the fragment or product ions are maintained separated from each other according to the ion mobilities of their precursor ions.

4. The method of claim 1, wherein in said first mode an axial electric field is applied along the fragmentation or reaction device so as to perform said step of urging the fragment or product ions through the fragmentation or reaction device such that the fragment or product ions are maintained separated from each other.

5. The method of claim 1, wherein in said first mode fragment or product ions derived from different precursor ions that have been separated by the ion mobility separator are maintained spatially separated from each other by one or more potential barriers or wells, and wherein said potential barriers or wells are moved along the fragmentation or reaction device so as to drive the fragment or product ions through the fragmentation or reaction device.

6. The method of claim 1, wherein in said second mode the ion mobility separated and mass filtered precursor ions are maintained separated from each other according to their ion mobilities as they are transmitted through the fragmentation or reaction device by applying an axial electric field along the fragmentation or reaction device that maintains the ion mobility separated and mass filtered precursor ions separated from each other according to their ion mobilities.

7. The method of claim 1, wherein in said second mode different precursor ions that have been separated by the ion mobility separator are maintained spatially separated from each other according to their ion mobilities by one or more potential barriers or wells, and wherein said potential barriers or wells are moved along the fragmentation or reaction device so as to drive the precursor ions through the fragmentation or reaction device.

8. The method of claim 1, wherein a fragment or product ion is associated to its precursor ions by:
 detecting the fragment or product ion;
 determining a drift time or range of drift times through the ion mobility separator of a precursor ion that led to said fragment or product ion being generated and detected;
 determining the mass to charge ratio or range of mass to charge ratios transmitted by said mass filter substantially at said drift time or range of drift times; and
 associating the fragment or product ion with a precursor ion having said mass to charge ratio or being within said range of mass to charge ratios.

9. The method of claim 1, wherein the fragment or product ions that are mass analysed and/or detected in the first mode are associated with elution times at which their respective precursor ions eluted from the ion mobility separator; wherein the precursor ions that are mass analysed and/or detected in the second mode are associated with their elution times from the ion mobility separator; and wherein the fragment or product ions detected in the first mode are associated with their respective precursor ions detected in the second mode by matching the elution times associated with the fragment or product ions with the elution times associated with the precursor ions.

10. The method of claim 9, further comprising identifying a precursor ion from one or more fragment or product ion determined to be associated with the precursor ion.

11. The method of claim 1, wherein the mass to charge ratios of the precursor ions transmitted by the mass filter vary as a function of ion mobility separator drift time in a continuous manner; or in a stepped manner.

12. The method of claim 1, wherein precursor ions are pulsed into the ion mobility separator in a plurality of pulses of precursor ions, wherein the mass to charge ratio transmittal window of the mass filter is scanned or stepped with drift time as the precursor ions from each pulse emerge from the ion mobility separator; and wherein the mass to charge ratio transmittal window of the mass filter is scanned or stepped with drift time in a different manner for each pulse of ions pulsed into the ion mobility separator.

13. A method of mass spectrometry comprising:
 separating precursor ions according to ion mobility by a Field Asymmetric Ion Mobility Separation (FAIMS) device;
 mass filtering precursor ions from a single separation cycle of the Field Asymmetric Ion Mobility Separation (FAIMS) device according to their mass to charge ratio with a mass filter, wherein the mass to charge ratios of the precursor ions transmitted by the mass filter vary with time; and
 repeatedly alternating between performing a first mode of operation and performing a second mode of operation on the ion mobility separated and mass filtered precursor ions from the single separation cycle of the Field Asymmetric Ion Mobility Separation (FAIMS) device;
 wherein performing the first mode of operation comprises:
  fragmenting or reacting the ion mobility separated and mass filtered precursor ions in a fragmentation or reaction device to form fragment or product ions;
  urging the fragment or product ions through the fragmentation or reaction device such that fragment or product ions derived from different precursor ions that have been separated according to their ion mobilities are maintained spatially separated from each other as they are urged through the fragmentation or reaction device; and
  detecting the fragment or product ions; and
 performing the second mode of operation comprises:
  the ion mobility separated and mass filtered precursor ions bypassing the fragmentation or reaction device, or being transmitted to the fragmentation or reaction device but being substantially not fragmented;
  maintaining the ion mobility separated and mass filtered precursor ions separated according to their ion mobilities as they bypass the fragmentation or reaction device or as they are transmitted through the fragmentation or reaction device; and
  detecting the ion mobility separated and mass filtered precursor ions; and
 the method further comprising:
 associating fragment or product ions detected when performing the first mode of operation to ion mobility separated and mass filtered precursor ions detected when performing the second mode of operation.

14. The method of claim 13, comprising setting the mass filter for transmitting plural precursor ions having a range of mass to charge ratios at any given drift time in said first mode and in said second mode.

15. The method of claim 13, wherein repeatedly alternating between performing the first mode of operation and performing the second mode of operation comprises performing multiple instances of the first mode of operation and performing multiple instances of the second mode of operation during the single separation cycle of the Field Asymmetric Ion Mobility Separation (FAIMS) device.

16. A mass spectrometer comprising:
 an ion mobility separator;

a mass filter;
fragmentation or reaction device;
an ion detector or mass analyser; and
a controller arranged and adapted to control the spectrometer to:
separate precursor ions according to ion mobility in said ion mobility separator;
mass filter precursor ions from a single separation cycle of the ion mobility separator according to their mass to charge ratio with said mass filter, wherein the mass to charge ratios of the precursor ions transmitted by the mass filter vary with time; and
repeatedly alternate between operating in a first mode of operation and operating in a second mode of operation on the ion mobility separated and mass filtered precursor ions from the single separation cycle of the ion mobility separator;
wherein operating the spectrometer in the first mode of operation comprises:
  fragmenting or reacting the ion mobility separated and mass filtered precursor ions in said fragmentation or reaction device to form fragment or product ions;
  urging the fragment or product ions through the fragmentation or reaction device such that fragment or product ions derived from different precursor ions that have been separated according to ion mobility are maintained spatially separated from each other as they are urged through the fragmentation or reaction device; and
  detecting the fragment or product ions; and
operating the spectrometer in the second mode of operation comprises:
  the ion mobility separated and mass filtered precursor ions bypassing the fragmentation or reaction device, or being transmitted to the fragmentation or reaction device but being substantially not fragmented;
  maintaining the ion mobility separated and mass filtered precursor ions separated according to their ion mobilities as they bypass the fragmentation or reaction device or as they are transmitted through the fragmentation or reaction device; and
  detecting the ion mobility separated and mass filtered precursor ions with a detector or mass analyser; and
the controller arranged and adapted to control the spectrometer to:
associate fragment or product ions detected when operating in the first mode of operation to ion mobility separated and mass filtered precursor ions detected when operating in the second mode of operation.

17. The mass spectrometer of claim 16,
wherein said controller is arranged and adapted to control the spectrometer to:
separate precursor ions using said ion mobility separator such that different precursor ions have different drift times through the ion mobility separator;
mass filter said ion mobility separated precursor ions with said mass filter, wherein the mass to charge ratios of the precursor ions transmitted by the mass filter vary as a function of the drift times of the precursor ions through the ion mobility separator.

18. The method of claim 1, comprising setting the mass filter is set for transmitting plural precursor ions having a range of mass to charge ratios at any given drift time in said first mode and in said second mode.

19. The method of claim 1, wherein repeatedly alternating between performing the first mode of operation and performing the second mode of operation comprises performing multiple instances of the first mode of operation and performing multiple instances of the second mode of operation during the single separation cycle of the ion mobility separator.

* * * * *